United States Patent Office

Plant Pat. 1,448

Patented Jan. 17, 1956

1,448

ROSE PLANT

John A. Armstrong, Ontario, Calif., assignor to Armstrong Nurseries, Inc., Ontario, Calif., a corporation of California No Drawing. Application August 24, 1953, Serial No. 376,766

1 Claim. (Cl. 47—61)

The present invention relates to a new and distinct variety of rose plant of the climbing hybrid tea class, which originated as a bud sport of the variety "Lowell Thomas" (Plant Patent No. 595), but which is distinguished from the latter parent variety by its climbing habit of growth. The new variety was discovered by me among cultivated plants of the variety "Lowell Thomas" which were being grown in the nursery rows on property under the control of my assignee and under my supervision, at Ontario, California.

At the time of my discovery, my attention was attracted to the new variety by the unusually vigorous and climbing habit of a particular plant of the variety "Lowell Thomas." Upon close examination thereof, I found that the parent plant had sported, and I thereupon promptly took steps to preserve, asexually reproduce and observe the sport for the purpose of determining whether its climbing habit was fixed and transmissible by asexual reproduction. This climbing habit was confirmed by asexual reproduction by budding as performed at Ontario, California, and said asexual reproduction has established that the climbing habit of growth of my new variety comes true to form and is transmissible through succeeding propagations.

The parent variety "Lowell Thomas" is a bush rose of the hybrid tea class, and is primarily notable for its hardiness and for the distinctive form and color of its flowers throughout their different stages of development. However, this bush variety, so far as I am aware, has never exhibited a climbing habit, and its growth has usually been that of the average strong bush rose which attains a height of from 3 to 3½ feet.

The new variety herein is substantially identical in all respects to its parent, except that it is definitely a climber, as evidenced by its vigorous and strong canes which attain a height at maturity of from 10 to 15 feet or more, and in addition, it is characterized by its habit of producing many more flowers in the spring than can usually be found at any one time on the parent bush variety "Lowell Thomas," with an intermittent flowering habit during the remainder of the growing season. The thorns of the new variety are the same as those on its parent, i. e., there are several thorns on each of the main stem, branches and new shoots, but no prickles or hairs.

In view of the general similarities between my new variety and its parent, except as noted above, it is unnecessary to specifically describe or illustrate the new variety in detail herein, since it otherwise substantially conforms to the detailed description and illustrations embodied in Plant Patent No. 595, dated July 13, 1943, to which reference may be readily had.

I claim:

A new and distinct variety of rose plant of the climbing hybrid tea class, substantially as described herein, characterized particularly as to novelty by being substantially identical with its parent variety "Lowell Thomas" (Plant Patent No. 595), but essentially being distinguished therefrom by its vigorous and climbing habit of growth as evidenced by its strong canes which attain a mature height of from 10 to 15 feet, at least, and by its habit of producing many more flowers in the spring than can usually be found at any one time on the parent variety.

No references cited.